(12) United States Patent
Park et al.

(10) Patent No.: US 9,757,049 B2
(45) Date of Patent: Sep. 12, 2017

(54) ELECTRODE AND DEVICE FOR DETECTING BIOSIGNAL AND METHOD OF USING THE SAME

(71) Applicant: Samsung Electronics Co., Ltd., Suwon-si (KR)

(72) Inventors: Sang Yun Park, Hwaseong-si (KR); Byung Hoon Ko, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 239 days.

(21) Appl. No.: 14/458,736

(22) Filed: Aug. 13, 2014

(65) Prior Publication Data
US 2015/0148646 A1 May 28, 2015

(30) Foreign Application Priority Data
Nov. 27, 2013 (KR) .................. 10-2013-0145052

(51) Int. Cl.
| | | |
|---|---|---|
| *A61B 5/0408* | (2006.01) | |
| *A61B 5/0478* | (2006.01) | |
| *A61B 5/0492* | (2006.01) | |
| *A61B 5/04* | (2006.01) | |

(Continued)

(52) U.S. Cl.
CPC .......... *A61B 5/04087* (2013.01); *A61B 5/04* (2013.01); *H05K 1/115* (2013.01); *H05K 1/118* (2013.01); *A61B 5/0478* (2013.01); *A61B 5/0492* (2013.01); *A61B 5/6832* (2013.01); *H05K 2201/0145* (2013.01); *H05K 2201/0329* (2013.01)

(58) Field of Classification Search
CPC .............. A61B 5/0492; A61B 5/04085; A61B 5/04087
USPC ........................................ 600/391–393, 396
See application file for complete search history.

(56) References Cited

U.S. PATENT DOCUMENTS

| | | | | |
|---|---|---|---|---|
| 3,977,392 A | * | 8/1976 | Manley ............... | A61B 5/0408 |
| | | | | 600/392 |
| 4,580,339 A | * | 4/1986 | Ioffe .................... | A61N 1/0456 |
| | | | | 29/825 |

(Continued)

FOREIGN PATENT DOCUMENTS

| | | |
|---|---|---|
| JP | 10-508227 A | 8/1998 |
| JP | 11-290286 A | 10/1999 |

(Continued)

OTHER PUBLICATIONS

Huigen, E. *Noise in biopotential recording using surface electrodes.* Diss. Ph. D. dissertation, Msc thesis, Delft Technical University, Nov. 2000. (38 Pages).

(Continued)

*Primary Examiner* — Lee S Cohen
(74) *Attorney, Agent, or Firm* — NSIP Law

(57) ABSTRACT

An electrode, a biosignal detecting device and a method of measuring a biosignal are provided. The electrode includes an ion conductive member configured to be attached to a body surface, a nonconductive member including a through hole and disposed on the ion conductive member, a conductive member disposed on the nonconductive member, and a nonpolarizable conductive member configured to electrically couple the ion conductive member to the conductive member.

21 Claims, 7 Drawing Sheets

(51) Int. Cl.
*H05K 1/11* (2006.01)
*A61B 5/00* (2006.01)

(56) References Cited

U.S. PATENT DOCUMENTS

| | | | | |
|---|---|---|---|---|
| 4,934,383 | A * | 6/1990 | Glumac | A61N 1/0456 607/152 |
| 5,402,780 | A * | 4/1995 | Faasse, Jr. | A61B 5/0408 29/877 |
| 7,486,980 | B2 * | 2/2009 | Lin | A61B 5/04087 600/391 |
| 7,668,580 | B2 * | 2/2010 | Shin | A61B 5/0416 600/372 |
| 8,332,009 | B2 * | 12/2012 | McLaughlin | A61B 5/0416 600/372 |
| 8,548,557 | B2 * | 10/2013 | Garstka | A61B 5/04087 600/391 |
| 8,548,558 | B2 * | 10/2013 | Dunagan | A61B 5/0408 600/382 |
| 8,718,740 | B2 * | 5/2014 | Virtanen | A61B 5/04087 600/372 |
| 9,333,333 | B2 * | 5/2016 | Bare | A61N 1/0456 |
| 9,433,380 | B1 * | 9/2016 | Bishay | A61B 5/04087 |
| 2008/0132772 | A1 * | 6/2008 | Lang | A61B 5/0408 600/392 |
| 2009/0043185 | A1 * | 2/2009 | McAdams | A61B 5/04087 600/372 |

FOREIGN PATENT DOCUMENTS

| | | |
|---|---|---|
| JP | 2002-529158 A | 9/2002 |
| JP | 2005-213455 A | 8/2005 |
| JP | 3887796 B2 | 7/2007 |
| KR | 10-2007-0043124 A | 4/2007 |
| KR | 10-0773447 B1 | 11/2007 |
| KR | 10-2010-0104404 A | 9/2010 |

OTHER PUBLICATIONS

Merletti, Roberto, et al. "Technology and instrumentation for detection and conditioning of the surface electromyographic signal: state of the art." *Clinical Biomechanics* vol. 24 (2009): 122-134.

* cited by examiner

ELECTRODE AND DEVICE FOR DETECTING BIOSIGNAL AND METHOD OF USING THE SAME

CROSS-REFERENCE TO RELATED APPLICATION

This application claims the benefit under 35 USC 119(a) of Korean Patent Application No. 10-2013-0145052 filed on Nov. 27, 2013, in the Korean Intellectual Property Office, the entire disclosure of which is incorporated herein by reference for all purposes.

BACKGROUND

1. Field

The following description relates to an electrode and a device for detecting biosignal, and a method of using such an electrode or device.

2. Description of Related Art

Biological systems frequently have electric activities associated with them. Thus, a human body may be considered a type of conductor through which the electric activities may be detected. A modest amount of current is generated throughout several portions of the body due to biological processes and movement of ions. Thus, physiological phenomena taking place internally within a human body may be measured by detecting current generated at various portions of the body or by detecting a change in the current in response to an external stimulus. For example, an electrocardiogram (ECG), an electromyogram (EMG), an electroencephalogram (EEG), a galvanic skin resistance (GSR), an electrooculogram (EOG), a body temperature, a pulse, a blood pressure, a body movement, and the like are biosignals that may be measured. Technology for analyzing and applying such measurements for various purposes of controlling diseases and general healthcare is currently under research. Detection of changes in such biosignals may require the use of an electrode for measuring a bioelectric signal within a living body. A conventional type of electrode that is applied to a body surface and detects a biopotential signal may include a hydrogel nonpolarizable electrode connector. The connector may include a snap in point-contact with the connector included in a system or a lead wire.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an electrode includes an ion conductive member configured to be attached to a body surface, a nonconductive member including a through hole and disposed on the ion conductive member, a conductive member disposed on the nonconductive member, and a nonpolarizable conductive member configured to electrically couple the ion conductive member to the conductive member.

The ion conductive member may include a substance having ionic conductivity and adhesiveness.

The ion conductive member may include a hydrogel.

The ion conductive member may include at least one hydrophilic polymer selected from the group consisting of collagen, gelatin, fibrin, alginic acid, hyaluronic acid, chitosan, and dextran, and at least one synthetic polymer selected from the group consisting of polyethylene glycol, poly(2-hydroxyethyl methacrylate) (PHEMA), poly(N,N-ethylaminoethly methacrylate), polyacrylic acid (PAAc), poly(lactide-caprolactone) (PLC), polyglycolide (PGA), polycaprolactone (PCL), poly(caprolactone-lactide) random copolymer (PCLA), poly(caprolactone-glycolide) random copolymer (PCGA), poly(lactide-glycolide) random copolymer (PLGA), and polyacrylamide.

The nonconductive member may include a substance having nonconductivity, an insulating property, and adhesiveness.

The nonconductive member may include at least one selected from the group consisting of polyethylene terephthalate (PET), nylon, polypropylene (PP), polyurethane (PU), polycarbonate (PC), and polyacrylate (PA).

The conductive member may be configured to electrically couple to the ion conductive member via the through hole of the nonconductive member.

The conductive member may include a substance having conductivity and adhesiveness.

The conductive member may include a conductive adhesive tape.

The nonpolarizable conductive member may include a substance comprising a metal/insoluble metal salt and having nonpolarizable conductivity.

The nonpolarizable conductive member may include at least one selected from the group consisting of sliver/silver chloride (Ag/AgCl), silver (Ag), copper (Cu), copper chloride (CuCl), tungsten (W), and stainless steel.

The nonpolarizable conductive member may have an impedance less than or equal to 3 kiloohms (kΩ) in a 10 hertz (Hz) interface.

The nonpolarizable conductive member may be formed by using an ink printing or coating method.

The nonpolarizable conductive member may be provided in a form of a panel or a film.

An interface between the conductive member and the nonpolarizable conductive member may be formed as silver/silver chloride-nickel (Ag/AgCl—Ni) or silver/silver chloride-carbon (Ag/AgCl—C).

The general aspect of the electrode may further include a support member configured to support the ion conductive member.

The support member may include at least one selected from the group consisting of soft rubber, polyethylene foam, polyurethane foam, urea foam, polyvinyl chloride (PVC) foam, polypropylene foam, polystyrene foam, polyvinyl acetate foam, melamine resin foam, and phenolic resin foam.

In another general aspect, a biosignal detecting device includes an electrode described above and a signal processing device including a terminal exposed or configured to be exposed on a surface of the signal processing device, an analog signal processor configured to process an analog signal transmitted from the terminal, an analog/digital (A/D) signal converter configured to convert the analog signal to a digital signal, and a digital signal processor configured to process the digital signal.

In another general aspect, a biosignal detecting device includes an electrode including an ion conductive member configured to adhere to a body surface, and a signal processing device comprising a terminal, a digital processor and a transceiver, the terminal being exposed or being configured to be exposed on an external surface of the signal processing device to provide a contact surface for attaching the electrode.

The terminal may be configured to electrically couple the signal processing device to the electrode via the contact surface, the digital signal processor may be configured to generate a digital signal based on a bioelectric signal detected by the electrode and received via the terminal, and the transceiver may be configured to transmit the digital signal.

In yet another general aspect, a method of measuring a biosignal involves attaching an electrode on a skin surface, the electrode comprising an ion conductive member configured to adhere to the skin surface, and attaching a signal processing device on the electrode, the signal processing device comprising a terminal, a digital signal processor and a transceiver, the terminal having a contact surface that adheres to an upper surface of the electrode.

The terminal may be configured to electrically couple the digital signal processor to the electrode via the contact surface; the digital signal processor is configured to produce a digital signal based on a signal received from the electrode; and the transceiver is configured to wirelessly transmit the digital signal.

Other features and aspects will be apparent from the following detailed description, the drawings, and the claims.

Figure 1:
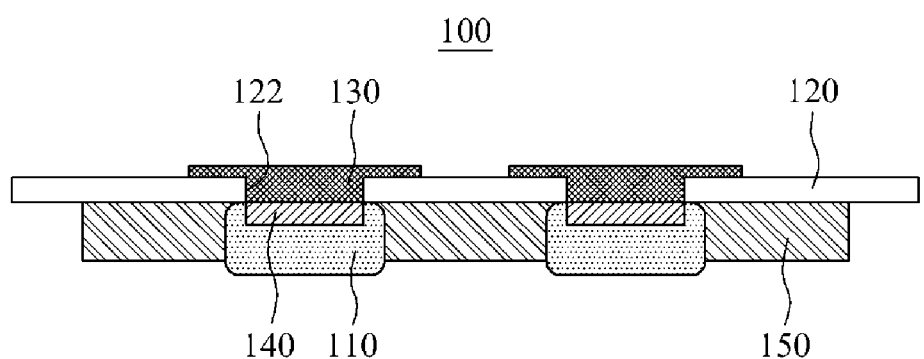
FIG. 1 is a cross-sectional view illustrating an example of an electrode for measuring a bioelectric signal of a body.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

An expression, "an element or a member (hereinafter referred to as a member) is 'connected to or coupled with' other member," as used herein may indicate that the member is "directly connected to or coupled with" the other member and also, that the member and the other member are "electrically connected to or coupled with" each other with another member therebetween.

An expression, "a member is disposed 'on' other member," as used herein may indicate that the member is in contact with the other member and also, that another member may present between the member and the other member.

An expression, "a member 'includes' a component," as used herein may indicate that the member may further include other components, barring an opposite polymer layer.

Figure 2:
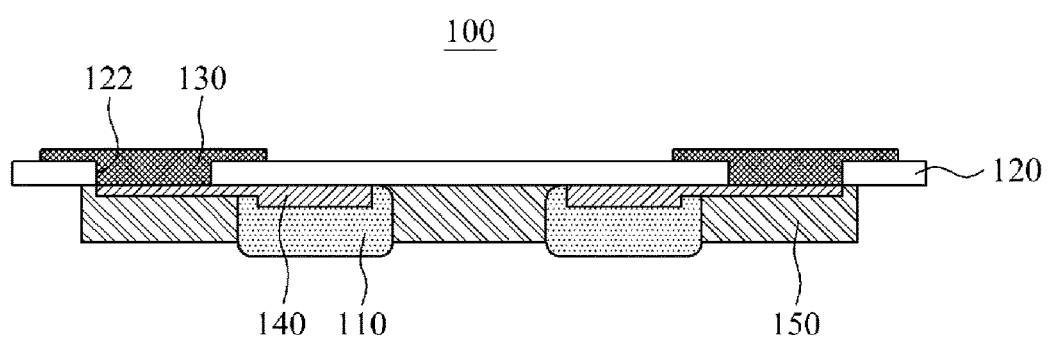
FIG. 2 is a cross-sectional view illustrating another example of an electrode.

FIGS. 1 and 2 are cross-sectional views illustrating examples of an electrode 100 for measuring a bioelectric signal of a body.

Referring to FIGS. 1 and 2, the electrode 100 includes an ion conductive member 110 to be attached to a surface of the body, a nonconductive member 120 formed on the ion conductive member 110 and including a through hole 122, a conductive member 130 formed on the nonconductive member 120, a nonpolarizable conductive member 140 to allow electrical coupling of the conductive member 130 and the ion conductive member 110, and a support member 150 to support the ion conductive member 110. However, the present disclosure is not limited hereto. For instance, according to another example, one or more elements illustrated in FIGS. 1 and 2 may be absent or additional elements may be provided in an electrode configured to measure a bioelectrical signal.

Referring to FIG. 1, the electrode 100 may be provided in an integral form in which the ion conductive member 110, the nonpolarizable conductive member 140, and the conductive member 130 are integrated based on the through hole 122 of the nonconductive member 120. Referring to FIG. 2, the electrode 100 may be provided in an integral form in which the nonpolarizable conductive member 140 and the conductive member 130 are integrated based on the through hole 122 of the nonconductive member 120.

The ion conductive member 110 may be formed using a substance having ionic conductivity and adhesiveness, such as, for example, a hydrogel. The ion conductive member 110 may deliver an electric signal through a surface-contact between the electrode 100 and a signal processing device, dissimilar to a point-contact between a projection and a recipient through which the electric signal may be transmitted. The hydrogel may be flexible to reduce inconveniences due to the ion conductive member 110 being directly attached to the body. Also, the hydrogel may be required to transmit a biosignal by being attached to the body and to suppress the generation of noise resulting from poor attachment. The hydrogel may have a suitable level of an adhesive strength that may not damage skin, cause pain during detachment, and/or dermal necrosis resulting from a long period of usage. The hydrogel may have a suitable level of an adhesive strength for skin without a need for the application of an additional adhesive. The adhesive strength for skin may be greater than or equal to approximately 50 grams/square centimeter ($g/cm^2$).

The ion conductive member 110 may be fabricated by polymerization of a polymer that has a high water content and a high degree of biocompatibility. The ion conductive member 110 may include a hydrophilic polymer and a synthetic polymer. The hydrophilic polymer may refer to a natural polymer that is naturally derived and includes at least one of collagen, gelatin, fibrin, alginic acid, hyaluronic acid, chitosan, and dextran. The synthetic polymer may include at least one of polyethylene glycol, poly(2-hydroxyethyl methacrylate) (PHEMA), poly(N,N-ethylaminoethly methacrylate), polyacrylic acid (PAAc), poly(lactide-caprolactone) (PLC), polyglycolide (PGA), polycaprolactone (PCL), poly(caprolactone-lactide) random copolymer (PCLA), poly(caprolactone-glycolide) random copolymer (PCGA), poly(lactide-glycolide) random copolymer (PLGA), and polyacrylamide.

The through hole 122 formed in the nonconductive member 120 may allow portions of the conductive member 130 and the ion conductive member 110 that are disposed on and below the nonconductive member 120 to be integrally connected.

The nonconductive member 120 may be formed using a substance having nonconductivity, an insulating property, and adhesiveness. The nonconductive member 120 may include at least one of polyethylene terephthalate (PET), nylon, polypropylene (PP), polyurethane (PU), polycarbonate (PC), and polyacrylate (PA).

Two conductive members 130 may be connected to a nonconductive member 120 and may fill the through hole 122 of the nonconductive member 120. The conductive member 130 may be formed using a substance having conductivity and adhesiveness. For example, the conductive member 130 may include a conductive adhesive tape. The conductive member 130 may include a substance that has a low electrochemical reactivity, such as, for example, carbon (C).

The nonpolarizable conductive member 140 may include at least one of sliver/silver chloride (Ag/AgCl), silver (Ag), copper (Cu), copper chloride (CuCl), tungsten (W), and stainless steel. Also, the nonpolarizable conductive member 140 may include a complex substance including a metal/insoluble metal salt such as Ag/AgCl. Thus, the nonpolarizable conductive member 140 may improve electrical coupling between the ion conductive member 110 and the conductive member 130.

The nonpolarizable conductive member 140 may be formed using a printing or coating method. For example, the nonpolarizable conductive member 140 may be formed by coating an Ag/AgCl paste on the conductive member 130. For example, the Ag/AgCl paste may include approximately 50% to 70% by weight of Ag and AgCl. The Ag/AgCl paste may be applied on a polymer matrix to form the nonpolarizable conductive member 140. The polymer matrix may be, for example, an epoxy. A thickness of the nonpolarizable conductive member 140 formed by the coating method may be in a range of tens of micrometers, and an overall thickness of the electrode 100 may also be in a range of tens of micrometers.

Nonpolarizability of the nonpolarizable conductive member 140 may be determined based on standards of the Association for the Advancement of Medical Instruments (AAMI) and may have an impedance lower than 3 kiloohms ($k\Omega$) in a 10 hertz (Hz) interface.

Also, the nonpolarizable conductive member 140 may be provided in a form of a panel or a film.

In the event that the nonpolarizable conductive member 140 is formed in the form of the panel or the film, a water component of the hydrogel of the ion conductive member 110 may not easily pass through the nonpolarizable conductive member 140. Accordingly, the nonpolarizable conductive member 140 may not be affected by a chemical change.

In an example, the electrode 100 of FIG. 1 may be provided in the integral form in which the ion conductive member 110, the nonpolarizable conductive member 140, and the conductive member 130 are integrated based on the through hole 122 of the nonconductive member 120. In another example, the electrode 100 of FIG. 2 may be provided in the integral form in which the nonpolarizable conductive member 140 and the conductive member 130 are integrated based on the through hole 122 of the nonconductive member 120.

In the event that the nonpolarizable conductive member 140 is provided in a form of an ink, the water component of the hydrogel of the ion conductive member 140 may be absorbed into between the nonpolarizable conductive member 140 formed as the ink and the conductive member 130. Accordingly, an electrochemical heterogeneous metal joint may be formed, thereby generating a gas between the ion conductive member 110, the nonpolarizable conductive member 140, and the conductive member 130. Alternatively, the ink and the conductive member 130 may be chemically changed. The electrode 100 of FIG. 2 may prevent an undesired chemical reaction caused by a chemical cell formed when moisture included in the ion conductive member 110 permeates the nonpolarizable conductive member 140 and the conductive member 130. To prevent the chemical change, an interface may be formed between the conductive member 130 and the nonpolarizable conductive member 140 using silver/silver chloride-nickel (Ag/AgCl—Ni) or silver/silver chloride-carbon (Ag/AgCl—C) that have a low electrochemical reactivity due to the heterogeneous metal joint.

The support member 150 may be formed to prevent the ion conductive member 110 from disengaging from the electrode 100. The support member 150 may include at least one of soft rubber, polyethylene foam, polyurethane foam, urea foam, polyvinyl chloride (PVC) foam, polypropylene foam, polystyrene foam, polyvinyl acetate foam, melamine resin foam, and phenolic resin foam. The support member 150 may also provide a frictional force required for the supporting.

Figure 3:
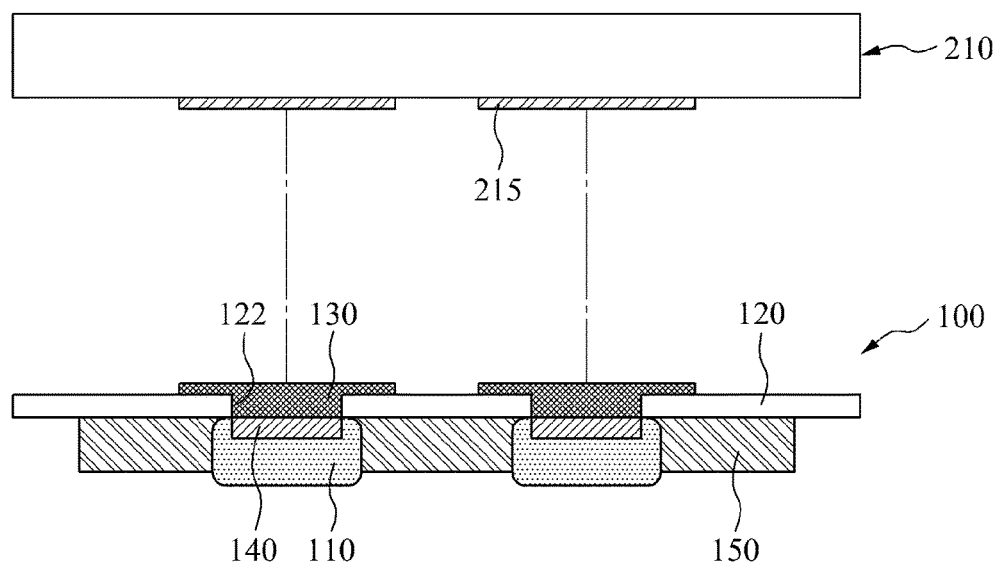
FIG. 3 is a cross-sectional view illustrating an example of a biosignal detecting device.
Figure 4:
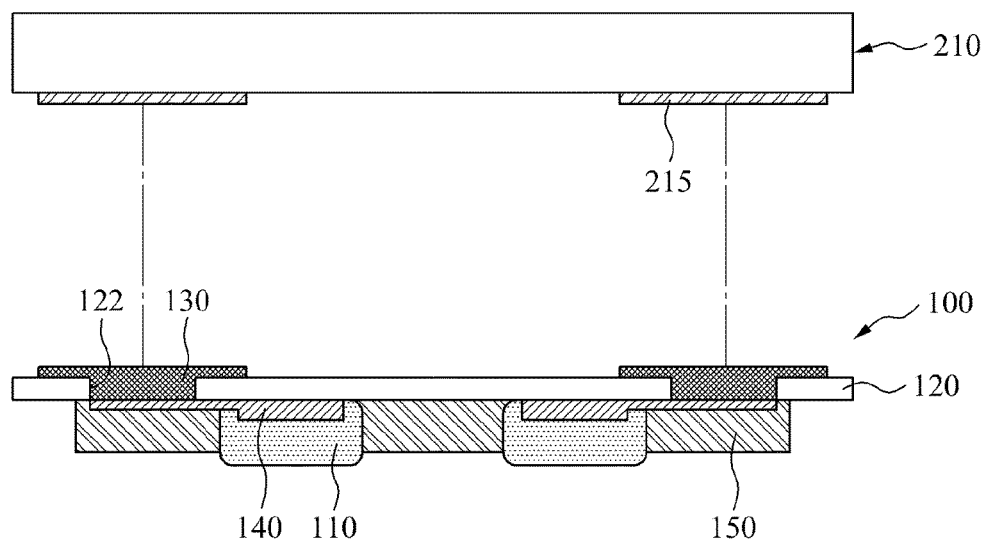
FIG. 4 is a cross-sectional view illustrating another example of a biosignal detecting device.

FIGS. 3 and 4 are cross-sectional views illustrating examples of a biosignal detecting device 200.

Referring to FIGS. 3 and 4, the biosignal detecting device 200 includes the electrode 100 and a signal processing device 210. The signal processing device 210 may include two terminals 215. The electrode 100 may include the ion conductive member 110 to be attached to a surface of a body, the nonconductive member 120 formed on the ion conductive member 110 and including a through hole 122, the conductive member 130 formed on the nonconductive member 120, the nonpolarizable conductive member 140 to allow electrical coupling between the conductive member 130 and the ion conductive member 110, and the support member 150 to support the ion conductive member 110. However, the present disclosure is not limited hereto. For instance, according to another example, one or more elements illustrated in FIGS. 3 and 4 may be absent or additional elements may be provided in a biosignal detecting device.

Figure 5:
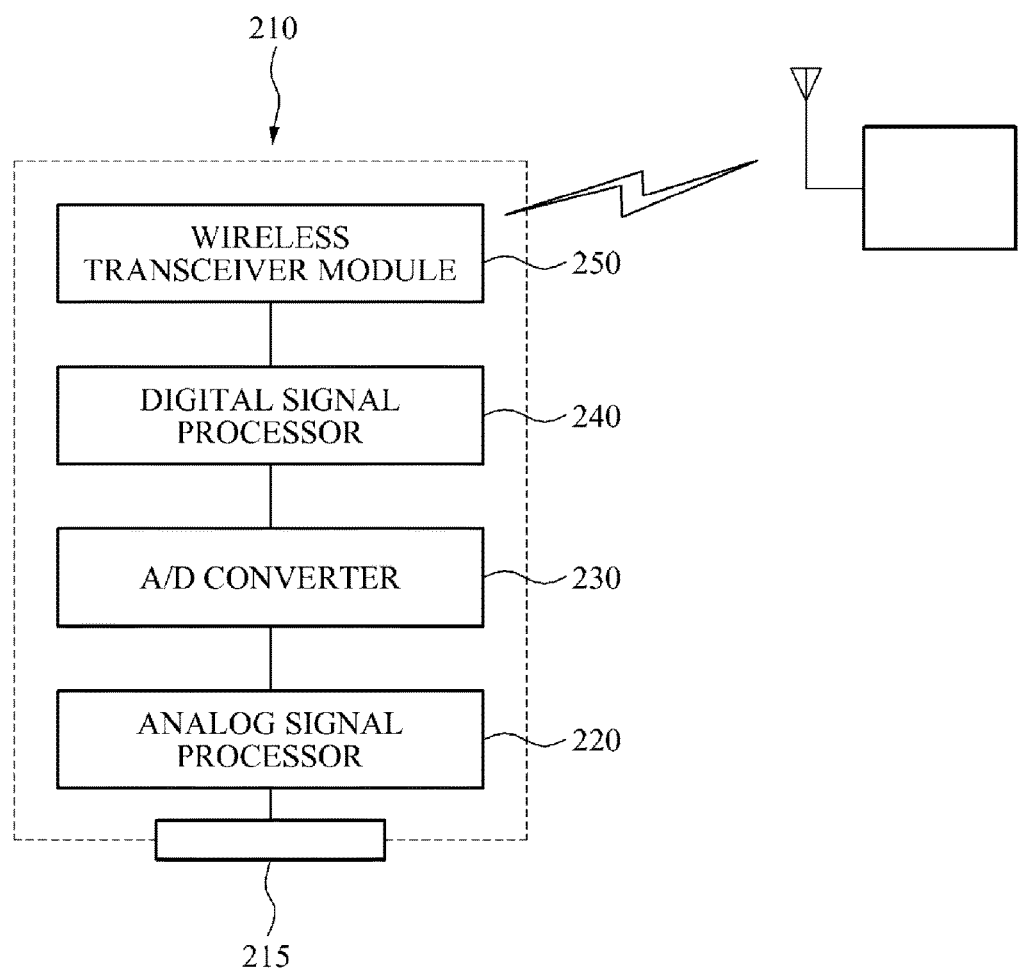
FIG. 5 is a diagram illustrating an example of a signal processing device included in a biosignal detecting device.

FIG. 5 is a diagram illustrating an example of a signal processing device 210 of the biosignal detecting device 200.

The signal processing device 210 includes the terminals 215 to be externally exposed, an analog signal processor 220 to process an analog signal transmitted from the terminals 215, an analog/digital (A/D) signal converter 230 to convert the analog signal to a digital signal, and a digital signal processor 240. However, the present disclosure is not limited hereto. For instance, according to another example, one or more elements illustrated in FIG. 5 may be absent or additional elements may be provided in a signal processing device.

The analog signal processor 220 may amplify or filter micro-electric signal of the body, or a signal in an analog form, transmitted from the terminals 215 and nay transmit the amplified or filtered signal to the A/D converter 230. The A/D converter 230 may convert the transmitted analog signal to a digital signal. The digital signal processor 240 may process the digital signal based on a preprogrammed method. A result of the processing may be transmitted to an external device through a wireless transceiver module 250 and stored in an internal memory.

The electrode 100 may be attached to a portion of a user at which a measurement is desired. The portion may be an ear, a finger, a toe, a neck, a wrist, or a forehead. The signal processing device 210 may be disposed on the electrode 100. Here, the terminals 215 of the signal processing device 210 may be electrically connected to the electrode 100. The terminals 215 and the electrode 100 may be connected to one another by a surface-contact through which the terminals 215 and the electrode 100 may be disposed on a flat contact surface and have a broader contact area and accordingly, resistance may be reduced due to the broad surface. Due to the surface-contact, a signal including a weak electric signal in the body may be effectively delivered to the terminals 215 of the signal processing device 210, a mechanical connection between the electrode 100 and the signal processing device 210 may be enabled, and a smooth electrical path may be provided. Accordingly, a signal-to-noise ratio (SNR) may be improved. Also, the biosignal detecting device 200 may be designed to be minimized in volume and used for an ultrathin sensor. The user may experience convenience due to the physical and electrical connection by attaching the signal processing device 210 to the electrode 100 without installing an additional connector.

In this example, the terminals 215 are exposed on an external surface of the signal processing device 210, and have a planar contact surface. The terminals may have a circular, oval, rectangular, or polygonal shape, and the size of the terminals may correspond to the size of the conductive members 130 or be slightly smaller or larger than that of the conductive members 130; however, the shape and size are not limited thereto. In another example, the terminals 215 may be provided with a protective covering that may be removed to expose the terminals 215 on the surface of the signal processing device 210.

The signal processing device 210 may have a wired or wireless connection to an external device. The signal processing device 210 may measure and deliver biosignal data including ECG, EMG, EEG, GSR, EOG, a body temperature, a pulse, and a body movement of the user while attached to the body of the user. The biosignal data may be analyzed to be used for disease control and health care.

According to one example, the overall shape of the signal processing device 210 may be that of a disk shape, a rectangular plate shape or other compact shape. Further, the wireless transceiver module 250 may be housed within the signal processing device 210 while the terminals 215 are provided on an external surface of the signal processing device 210. By housing the wireless transceiver 250 within the signal processing device 210 on which the terminals 215 are provided, it is possible to eliminate wire connections in the biosignal detecting device, providing convenience to the wearer. The electrodes can, for example, be worn under clothing without a wired connection to an external device. However, the present disclosure is not limited thereto.

Figure 6:
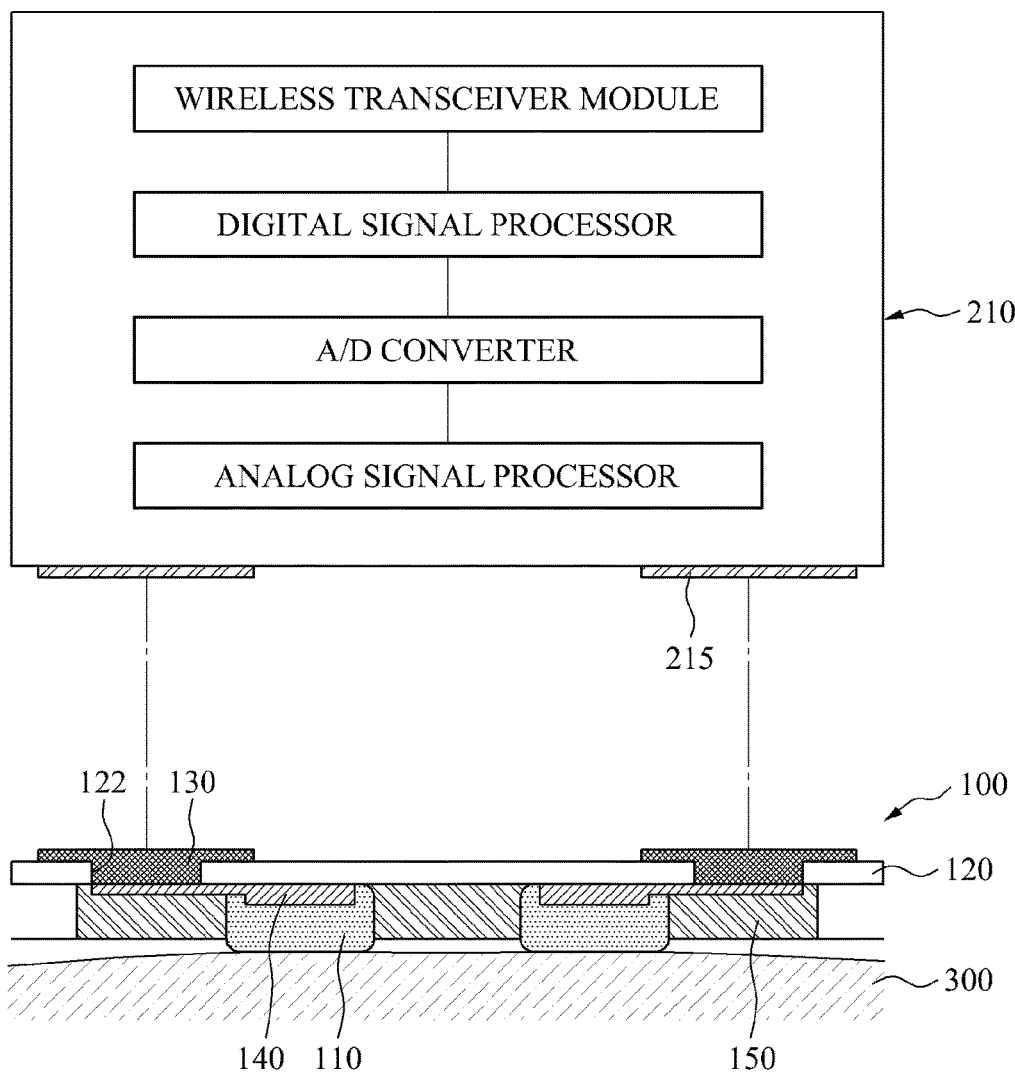
FIG. 6 is a diagram illustrating an example of a biosignal detecting device.

FIG. 6 is a diagram illustrating an example of the biosignal detecting device 200.

Referring to FIG. 6, the biosignal detecting device 200 includes an electrode 100 for measuring a bioelectric signal of a body and a signal processing device 210.

The electrode 100 may be attached to a portion 300 of the body of the user at which a measurement is to be performed. For example, the ion conductive member 110 of the electrode 100 may be attached to the portion 300. The portion 300 may be an ear, a finger, a toe, a neck, a wrist, a chest, a torso, or a forehead of the user. Although an electrolytic cream including an electrolyte may be used to attach the electrode 100 to the body, the ion conductive member 110 of the electrode 100 may be easily adhered to the portion 300 without using the electrolytic cream because the ion conductive member 110 in a direct contact with the portion 300 possesses ionic conductivity and adhesiveness.

The electrode 100 includes the ion conductive member 110 to be attached to a surface of the body, the nonconductive member 120 to be formed on the ion conductive member 110 and including the through hole 122, the conductive member 130 to be formed on the nonconductive member 120, the nonpolarizable conductive member 140 to allow electric coupling between the conductive member 130 and the ion conductive member 110, and the support member 150 to support the ion conductive member 110.

The ion conductive member 110 may be formed using a substance, for example, hydrogel, having ionic conductivity and adhesiveness. The ion conductive member 110 may deliver an electric signal through a surface-contact between the electrode 100 and the signal processing device 210, dissimilar to a point-contact between a projection and a recipient through which the electric signal may be transmitted.

The ion conductive member 110 may be fabricated by polymerization of a polymer that has a high content of water and is highly biocompatible. The ion conductive member 110 may include a hydrophilic polymer and a synthetic polymer. The hydrophilic polymer may refer to a natural polymer that is naturally derived and include at least one of collagen, gelatin, fibrin, alginic acid, hyaluronic acid, chitosan, and dextran. The synthetic polymer may include at least one of polyethylene glycol, PHEMA, poly(N,N-ethylaminoethly methacrylate), PAAc, PLC, PGA, PCL, PCLA, PCGA, PLGA, and polyacrylamide.

The through hole 122 formed in the nonconductive member 120 may allow portions of the conductive member 130 and the ion conductive member 110 that are disposed on and below the nonconductive member 120 to be integrally connected.

The nonconductive member 120 may be formed using a substance having nonconductivity, an insulating property, and adhesiveness. The nonconductive member 120 may include at least one of PET, nylon, PP, PU, PC, and PA.

The conductive member 130 may connect the nonconductive member 120 separated by the through hole 122. The conductive member 130 may be formed using a substance having conductivity and adhesiveness. For example, the conductive member 130 may include a conductive adhesive tape. The conductive member 130 may be a substance that has a low electrochemical reactivity, such as, for example, carbon (C).

The nonpolarizable conductive member 140 may include at least one of Ag/AgCl, Ag, Cu, CuCl, W, and stainless steel. Also, the nonpolarizable conductive member 140 may include a complex substance including a metal/insoluble metal salt such as Ag/AgCl. Thus, the nonpolarizable conductive member 140 may improve electrical coupling of the ion conductive member 110 and the conductive member 130.

The nonpolarizable conductive member 140 may be formed using a printing or coating method. For example, the nonpolarizable conductive member 140 may be formed by coating an Ag/AgCl paste on the conductive member 130.

The support member 150 may be formed to prevent the ion conductive member 110 from disengaging from the electrode 100. The support member 150 may include at least one of soft rubber, polyethylene foam, polyurethane foam, urea foam, PVC foam, polypropylene foam, polystyrene foam, polyvinyl acetate foam, melamine resin foam, and phenolic resin foam. The support member 150 may also provide a frictional force required for the supporting.

The signal processing device 210 includes the terminals 215 to be externally exposed, the analog signal processor 220 to process an analog signal transmitted from the terminals 215, the A/D signal converter 230 to convert the analog signal to a digital signal, and the digital signal processor 240.

The signal processing device 210 may be attached to the electrode 100. Here, the terminals 215 of the signal processing device 210 may be electrically connected to the electrode 100. The terminals 215 and the electrode 100 may be connected to one another by a surface-contact through which the terminals 215 and the electrode 100 may be disposed on a flat contact surface and have a broader contact area and accordingly, resistance may be reduced due to the broad surface. Due to the surface-contact, a signal including a weak electric signal in the body may be effectively delivered to the terminals 215 of the signal processing device 210, a mechanical connection between the electrode 100 and the signal processing device 210 may be enabled, and a smooth electrical path may be provided. Accordingly, a signal-to-noise ratio (SNR) may be improved. However, the present disclosure is not limited hereto. For instance, according to another example, one or more elements illustrated in FIG. 6 may be absent or additional elements may be provided in a biosignal detecting device 200.

Referring to FIG. 6, the analog signal processor 220 may amplify or filter a micro-electric signal of the body, or a signal in an analog form, transmitted from the terminals 215 and transmit the amplified or filtered signal to the A/D converter 230. The A/D converter 230 may convert the transmitted analog signal to a digital signal, and the digital signal processor 240 may process the digital signal based on a preprogrammed method. A result of the processing may be transmitted to an external device through the wireless transceiver module 250 and stored in an internal memory.

The signal processing device 210 may have a wired or wireless connection to an external device. The signal processing device 210 may measure and deliver biosignal data including ECG, EMG, EEG, GSR, EOG, a body temperature, a pulse, and a body movement of the user while attached to the body of the user. The biosignal data may be used for various purposes of disease control and healthcare.

The electrode 100 and the signal processing device 210 may be connected to one another by a surface-contact and transmit an electric signal using a broad surface, dissimilar to a point-contact between a projection and a recipient through which the electric signal may be transmitted. Accordingly, the connection between the terminals 215 and the signal processing device 210 may be stably maintained, a desired signal may be delivered with a low amount of current, and relatively little noise may occur due to the stable connection. Accordingly, an SNR may be improved.

Figure 7:
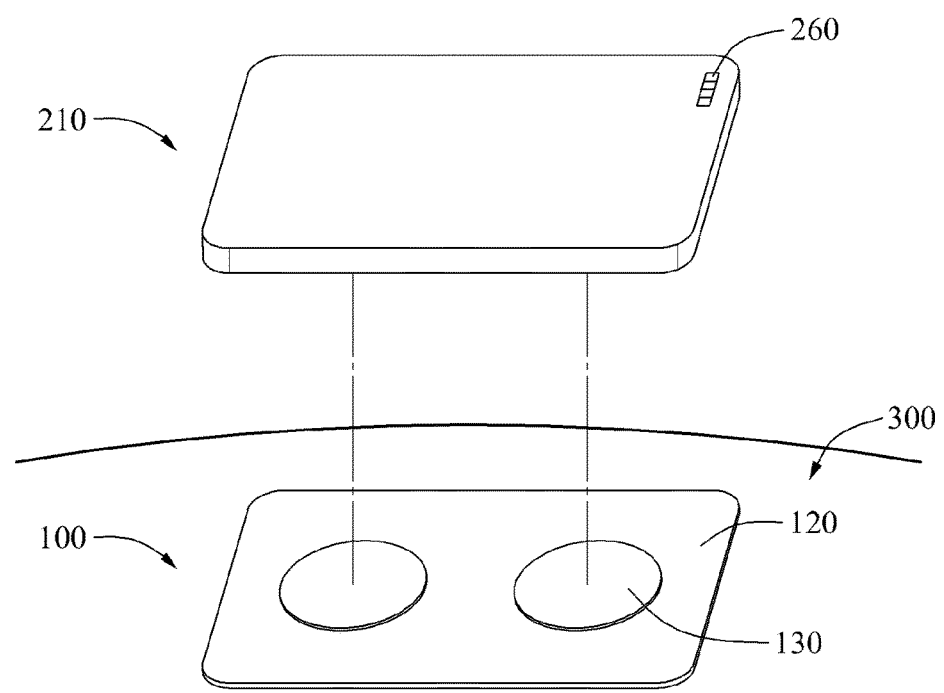
FIG. 7 is a diagram illustrating another example of a biosignal detecting device.

FIG. 7 is a perspective view of an example of a biosignal detecting device 200. The biosignal detecting device 200 of FIG. 7 may have the structure of the biosignal detecting device 200 illustrated in FIG. 6, and the description provided with respect to FIG. 6 applies to the illustrated example of FIG. 7.

Referring to FIG. 7, the biosignal detecting device 200 includes an electrode 100 for measuring a bioelectric signal that may be applied to a skin surface 300 and a signal processing device 210 that may be applied to an upper surface of the electrode 100.

The skin may correspond to a portion of an ear, a finger, a toe, a neck, a wrist, chest, a torso, or a forehead of the user. The electrode 100 may be thin, flat and flexible and may be easily applied to the surface of the skin 300 by pressing the electrode 100 on the skin with a hand, for example. The ion conductive member 110 may allow adhesion to the skin surface 300, without the use of any additional adhesives.

The signal processing device 210 may include terminals 215 on its lower surface, and the terminals 215 may be aligned to the conductive members 130 provided on the upper surface of the electrode 100 for adhesion. After applying the electrode 100 at a desired location of the body, the signal processing device 210 may be applied on the electrode 100 so that the conductive members 130 contact and adhere to the terminals 215. In an example, the conductive members 130 may have enough adhesion to hold the signal processing device 210 in place without the use of any additional adhesives. In this example, the conductive members 130 have a circular shape and the terminals 215 have a circular shape of corresponding size. However, the shape of the conductive members 130 and the terminals 215 are not limited thereto; further, in another example, the conductive members 130 may have a larger or a smaller area than the terminals 215, or even be fused into one large area. Likewise, the number of nonconductive members and terminals may vary based on application.

After applying the signal processing device 210, a biosignal may be transmitted by the signal processing device 210 based on the bioelectric signal of the body detected by the electrode 100. In one example, the attachment of the signal processing device 210 may trigger the operation of the signal processing device 210 and the transmission of the biosignal data to an external device. In the illustrated example, a switch 260 allows the biosignal processing device 210 to be turned on in order to transmit the biosignal data. The biosignal data may include ECG, EMG, EEG, GSR, EOG, a body temperature, a pulse, and a body movement of the user. However, the types of biosignal data are not limited thereto.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An electrode comprising:
a support member;
an ion conductive member configured to be attached to a body surface, wherein the ion conductive member is embedded in a portion of the support member and is exposed in a direction of the body surface;
a nonconductive member disposed directly upon the support member and the ion conductive member, wherein the nonconductive member comprises a through hole that is offset from the portion of the support member such that the through hole and the portion do not overlap;
a conductive member disposed directly upon the nonconductive member, wherein the conductive member comprises a substance having conductivity and adhesiveness; and
a nonpolarizable conductive member configured to electrically couple the ion conductive member to the conductive member, wherein the nonpolarizable conductive member overlaps the through hole and the portion of the support member,
wherein the support member extends integrally to support the nonpolarizable conductive member and the ion conductive member.

2. The electrode of claim 1, wherein the ion conductive member comprises a substance having ionic conductivity and adhesiveness.

3. The electrode of claim 1, wherein the ion conductive member comprises a hydrogel.

4. The electrode of claim 1, wherein the ion conductive member comprises:
at least one hydrophilic polymer selected from the group consisting of collagen, gelatin, fibrin, alginic acid, hyaluronic acid, chitosan, and dextran; and
at least one synthetic polymer selected from the group consisting of polyethylene glycol, poly(2-hydroxyethyl methacrylate) (PHEMA), poly(N,N-ethylaminoethly methacrylate), polyacrylic acid (PAAc), poly(lactide-caprolactone) (PLC), polyglycolide (PGA), polycaprolactone (PCL), poly(caprolactone-lactide) random copolymer (PCLA), poly(caprolactone-glycolide) random copolymer (PCGA), poly(lactide-glycolide) random copolymer (PLGA), and polyacrylamide.

5. The electrode of claim 1, wherein the nonconductive member comprises a substance having nonconductivity, an insulating property, and adhesiveness.

6. The electrode of claim 1, wherein the nonconductive member comprises at least one selected from the group consisting of polyethylene terephthalate (PET), nylon, polypropylene (PP), polyurethane (PU), polycarbonate (PC), and polyacrylate (PA).

7. The electrode of claim 1, wherein the conductive member is configured to electrically couple to the ion conductive member via the through hole of the nonconductive member.

8. The electrode of claim 1, wherein the conductive member comprises a conductive adhesive tape.

9. The electrode of claim 1, wherein the nonpolarizable conductive member comprises a substance comprising a metal/insoluble metal salt and having nonpolarizable conductivity.

10. The electrode of claim 1, wherein the nonpolarizable conductive member comprises at least one selected from the group consisting of sliver/silver chloride (Ag/AgCl), silver (Ag), copper (Cu), copper chloride (CuCl), tungsten (W), and stainless steel.

11. The electrode of claim 1, wherein the nonpolarizable conductive member has an impedance less than or equal to 3 kiloohms (kΩ) in a 10 hertz (Hz) interface.

12. The electrode of claim 1, wherein the nonpolarizable conductive member is formed by using an ink printing or coating method.

13. The electrode of claim 1, wherein the nonpolarizable conductive member is provided in a form of a panel or a film.

14. The electrode of claim 1, wherein an interface between the conductive member and the nonpolarizable conductive member is formed as silver/silver chloride-nickel (Ag/AgCl—Ni) or silver/silver chloride-carbon (Ag/AgCl—C).

15. The electrode of claim 1, wherein the support member comprises at least one selected from the group consisting of soft rubber, polyethylene foam, polyurethane foam, urea foam, polyvinyl chloride (PVC) foam, polypropylene foam, polystyrene foam, polyvinyl acetate foam, melamine resin foam, and phenolic resin foam.

16. The electrode of claim 1, further comprising:
an interface between the conductive member and the nonpolarizable conductive member, the interface comprising silver and having a low electrochemical reactivity,
wherein the nonpolarizable conductive member is provided in the form of an ink.

17. A biosignal detecting device comprising:
an electrode comprising
a support member;
an ion conductive member configured to adhere to a body surface, wherein the ion conductive member is embedded in a portion of the support member and is exposed in a direction of the body surface;
a nonconductive member disposed directly upon the support member and the ion conductive member, wherein the nonconductive member comprises a through hole that is offset from the portion of the support member such that the through hole and the portion do not overlap;
a conductive member disposed directly upon the nonconductive member; and
a nonpolarizable conductive member configured to electrically couple the ion conductive member to the conductive member, wherein the nonpolarizable conductive member overlaps the through hole and the portion of the support member,
wherein the support member extends integrally to support the nonpolarizable conductive member and the ion conductive member; and
a signal processing device comprising a terminal, a digital processor, and a transceiver, wherein the terminal is configured to be exposed on an external surface of the signal processing device to provide a contact surface for attaching the electrode.

18. The biosignal detecting device of claim 17, further comprising:
an analog signal processor configured to process an analog signal transmitted from the terminal; and
an analog/digital (ND) signal converter configured to convert the analog signal to a digital signal,
wherein the digital signal processor is configured to process the digital signal.

19. The device of claim 17, wherein the terminal is configured to electrically couple the signal processing device to the electrode via the contact surface, the digital signal processor is configured to generate a digital signal based on a bioelectric signal detected by the electrode and received via the terminal, and the transceiver is configured to transmit the digital signal.

20. A method of measuring a biosignal, the method comprising:
attaching an electrode on a skin surface, the electrode comprising
a support member;
an ion conductive member configured to adhere to the skin surface, wherein the ion conductive member is embedded in a portion of the support member and is exposed in a direction of the body surface;
a nonconductive member disposed directly upon the support member and the ion conductive member, wherein the nonconductive member comprises a through hole that is offset from the portion of the support member such that the through hole and the portion do not overlap;
a conductive member disposed directly upon the nonconductive member; and
a nonpolarizable conductive member configured to electrically couple the ion conductive member to the conductive member, wherein the nonpolarizable conductive member overlaps the through hole and the portion of the support member,
wherein the support member extends integrally to support the nonpolarizable conductive member and the ion conductive member; and
attaching a signal processing device on the electrode, the signal processing device comprising a terminal, a digital signal processor, and a transceiver, the terminal having a contact surface that adheres to an upper surface of the electrode.

21. The method of claim 20, further comprising
electrically coupling, by the terminal, the digital signal processor to the electrode via the contact surface;
producing, by the digital signal processor, a digital signal based on a signal received from the electrode; and
wirelessly transmitting, by the transceiver, the digital signal.

* * * * *